United States Patent [19]

Moonka

[11] Patent Number: 5,290,244
[45] Date of Patent: Mar. 1, 1994

[54] SYRINGE AND NEEDLE WITH GUIDE WIRE FOR CANNULATION OF CENTRAL VEINS

[76] Inventor: Dilip Moonka, 12 Eusden Dr., Aston, Pa. 19014

[21] Appl. No.: 895,308

[22] Filed: Jun. 8, 1992

[51] Int. Cl.⁵ ..................... A61M 5/32; A61M 25/01; A61M 5/178
[52] U.S. Cl. ..................... 604/164; 604/158; 604/169; 604/218; 604/239; 604/187
[58] Field of Search ............... 604/239, 218, 164, 169, 604/158, 167, 187

[56] References Cited

U.S. PATENT DOCUMENTS

| | | | |
|---|---|---|---|
| 4,758,218 | 7/1988 | Kiefer et al. | 604/218 X |
| 4,824,433 | 4/1989 | März et al. | 604/164 X |
| 4,935,008 | 6/1990 | Lewis | 604/52 |
| 5,100,383 | 3/1992 | Lichtenstein | 604/96 |

FOREIGN PATENT DOCUMENTS 0524404  5/1956  Canada ................... 604/239

Primary Examiner—Randall L. Green
Assistant Examiner—D. Willse
Attorney, Agent, or Firm—Norman E. Lehrer

[57] ABSTRACT

A hub member interconnecting a needle and syringe includes a side port having a bore therein that intersects the needle bore at an acute angle. A guide wire which is intended to be introduced into a human blood vessel extends from the exterior of the side port, through the side port bore and terminates within the needle bore. An O-ring located within the side port seals around the guide wire to prevent communication between the needle bore and the exterior of the side port when the guide wire is at rest.

5 Claims, 1 Drawing Sheet

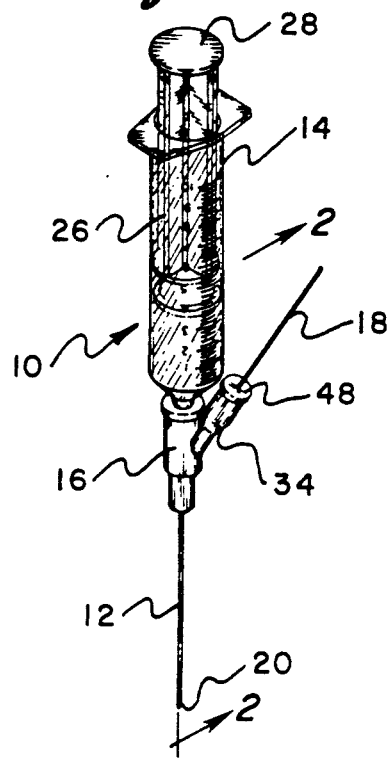
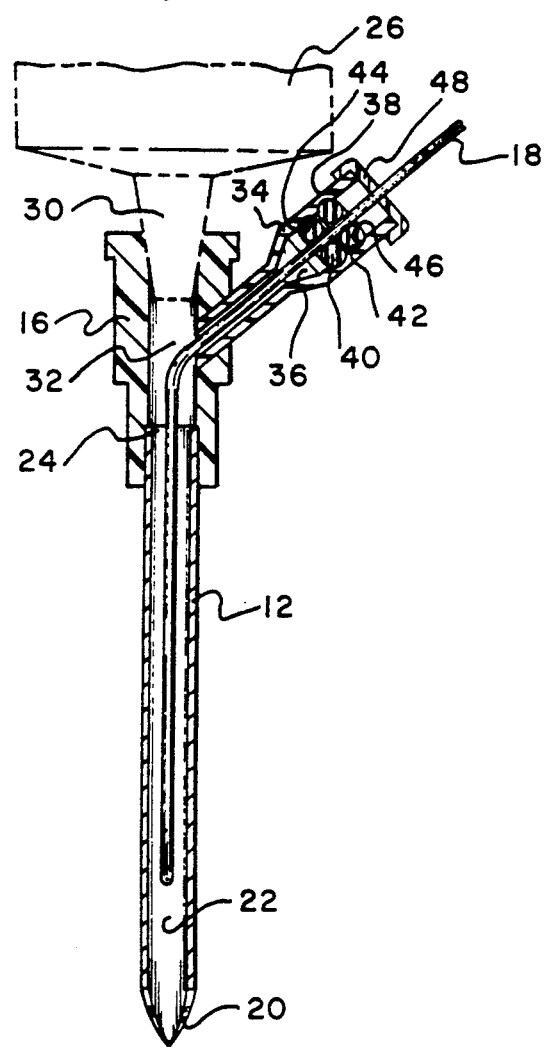
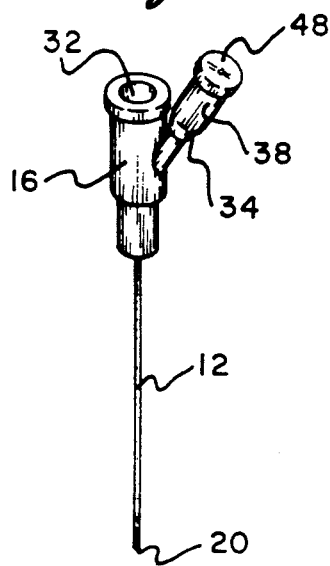

SYRINGE AND NEEDLE WITH GUIDE WIRE FOR CANNULATION OF CENTRAL VEINS

BACKGROUND OF THE INVENTION

The present invention is directed toward a combined syringe and needle and, more particularly, to such a combination which further combines a guide wire therewith for introducing the guide wire into human blood vessels.

The arrangement of the present invention is particularly designed for the easier cannulation of central veins such as the internal jugular, subclavian and femoral veins. Cannulation is done to provide a reliable portal for the administration of intravenous drugs and fluids to patients with poor peripheral veins, those requiring potential caustic drugs or those so ill that their illness requires a very reliable portal for drugs such as in the case with patients requiring vasopressor drips to maintain blood pressure.

Central veins may also be cannulated for the placement of pulmonary artery catheters for the continuous monitoring of cardiac output and pulmonary artery pressures. Irrespective of the ultimate reason for the cannulation of central veins, the veins are all currently cannulated by essentially the same procedure which is generally referred to as the J-Wire internal jugular catheterization technique.

For all central line placements, the patient is placed in a supine position and the area of skin overlying the vein to be cannulated is sterilized with an antiseptic solution. Multiple sterile drapes are placed around the chosen site to prevent bacteria from non-sterilized areas from coming into the sterile field and to provide a sterile surface to place some of the instruments that will be used. The site of the central vein is approximated by skin surface landmarks and a large bore needle with attached syringe is used to empirically aspirate around this site until the vein is found.

As is well known in the art, the physician aspirates by drawing back on the plunger of the syringe and feels the force needed to do so. If a large force is required to withdraw the syringe, a vein has not been found even though one may be present in the vicinity. The physician knows that he has penetrated the vein when blood flows easily into the syringe as he aspirates. Obviously, this procedure requires that the needle and syringe be an airtight system which is not open to the atmosphere or the syringe plunger could always be easily withdrawn whether or not the needle has penetrated a vein. It would, therefore, be extremely difficult, if not impossible, for the physician to locate the vein.

Once the vein is found, the physician must disengage and remove the syringe barrel from the needle. This process necessarily involves pulling, twisting and/or turning the syringe barrel in relation to the needle which may cause substantial manipulation of the needle while it is in place within the vein. This can often result in trauma to the vein and unnecessary discomfort to the patient. Moreover, this manipulation of the needle may result in its movement from the initial puncture site. That is, the needle can be pulled back out of the vein or it may accidentally be advanced too far causing it to exit the backside of the vein. Accordingly, it is necessary for the physician to manually and steadily hold or "freeze" the needle while removing the syringe from the hub of the needle. This must be done very carefully in order to avoid any movement of the needle itself.

After the syringe is removed, an elongated flexible guide wire is then inserted into the now open hub of the needle and is threaded through the needle into the vein. These guide wires are usually and conventionally comprised of a wound metal wire having its forward end bent back slightly in the form of a "J."

With the flexible guide wire in place, the needle is then slid out of the vein and over the length of the guide wire and discarded. This is done while the wire remains lodged with one end in the vein and the other end protruding from the vein and outside the skin. An elongated tubular catheter made of a soft rubber or plastic is then slid over the protruding end of the guide wire into the vein and the wire is then removed. Intravenous tubing is connected t the catheter and central venous access has then been obtained.

Difficulty in this conventional procedure arises in several distinct but related areas. The first, as suggested above, is when removing the syringe from the hub of the needle which can cause dislodgment of the needle. The second is in holding the needle absolutely still while placing the syringe down on the sterile surface and grasping the end of the guide wire. A guide wire must then be inserted into the open hub of the needle and through the needle toward the vein. During these procedures, it is not unusual to dislodge the needle from the vein. If this happens, the guide wire will not be able to slide into the vein and the physician will feel resistance as he tries to slide the wire through the needle. Upon such an occurrence, the wire must be removed from the needle, the syringe reattached to the needle and an attempt must be made to "find" the vein again. Once the vein has again been located, the process of trying to thread the wire into the vein is repeated.

The foregoing is a problem which is well known and recognized when using this conventional catheterization technique. Attempts have been proposed in the past to provide improved syringes in order to overcome the problem of dislodging the needle. While these devices may offer partial solutions, to Applicant's knowledge, they have not entirely solved the problem.

One such proposed solution is illustrated in U.S. Pat. No. 4,813,938 which describes a syringe sold under the trademark Safety Syringe by Arrow International, Inc., of Reading, Pa. The Safety Syringe includes a continuous passageway which extends entirely through the center of the needle and through the entire syringe including the plunger and plunger handle. With the use of the Safety Syringe, it is not necessary to remove the syringe barrel from the needle. Rather, once the vein is found, the safety wire is introduced into the rear of the syringe plunger handle and entirely through the central passageway, through the needle and into the vein.

While the Safety Syringe would appear to obviate the problem of dislodging the needle since the syringe barrel need not be removed, in practice it apparently does not do so. This results from the fact that the doctor must attempt to maintain the entire needle and syringe combination absolutely still while locating the guide wire and forcing it entirely through the center of the syringe and needle. Because of the length of the syringe body and plunger and the fact that the physician must manipulate the guide wire at the very end thereof, it is difficult to maintain the entire arrangement absolutely still. The physician loses his "feel" for the location of the needle and even a small movement at the end of the syringe can cause a significant movement at the tip of the needle.

Another arrangement which has been proposed is a double lumen introducing needle described in U.S. Pat. No. 4,935,008. This patent utilizes a hub casing between the syringe and the needle which includes a side port having a bore which intersects the bore of the needle at an acute angle. The end of the bore in the side port is normally closed with a rubber-like cap so that the needle syringe arrangement is airtight for the reasons discussed above. Once the needle is properly located in the vein, it is not necessary to remove the syringe barrel from the needle. Rather, the guide wire is forced through the cap at the end of the side port, through the needle bore and into the vein.

Again, while the device shown in U.S. Pat. No. 4,935,008 may, in principle, appear to be an improvement over the prior art practice, it does not appear to entirely solve the problem. More specifically, the guide wire must be forced through the end cap which can cause the needle to move, thereby dislodging the tip thereof. Furthermore, a guide wire that is sharp enough to pierce the rubber diaphragm of the cap could potentially pierce the vein as it is threaded into it. Even further, if for some reason the guide wire does not slide smoothly into the vein and has to be withdrawn, it must be entirely removed from the side port so that a new cap can be placed thereon. This is necessary to ensure an airtight seal during the aspiration step needed to locate the vein.

SUMMARY OF THE INVENTION

The purpose of the present invention is to overcome all of the problems of the prior art discussed above and to provide a syringe, needle and guide wire combination which allows a physician to more quickly and safely insert the guide wire into a patient's central vein. According to the invention, a hub member interconnects the needle and syringe and includes side port associated therewith. A bore within the side port intersects the needle bore at an acute angle. A guide wire which is intended to be introduced into a human blood vessel extends from the exterior of the side port, through the side port bore and terminates within the needle bore. An O-ring located within the side port seals around the guide wire to prevent communication between the needle bore and the exterior of the side port when the guide wire is at rest.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a perspective view of a combined needle, syringe and guide wire combination constructed in accordance with the principles of the present invention;

FIG. 2 is a cross-sectional view taken through the line 2—2 of FIG. 1, and

FIG. 3 is a perspective view of the needle and hub casing with side port which forms a part of the invention.

DETAILED DESCRIPTION OF THE PREFERRED EMBODIMENT

Referring now to the drawings in detail wherein like reference numerals have been used throughout the various figures to designate like elements, there is shown in FIG. 1 a combined needle, syringe and guide wire arrangement constructed in accordance with the principles of the present invention and designated generally as 10. The arrangement 10 is comprised essentially of four parts: a needle 12, syringe 14, a hub member 16 and a guide wire 18.

The needle 12 is of substantially conventional type having a sharpened point 20 at the lower end thereof. Needle 12 also has a hollow bore 22 extending from the end 20 through the center of the needle to the upper or hub end 24.

The syringe 14 is also of substantially conventional construction. Syringe 14 includes a syringe barrel 26 and a plunger 28 which fits therein in a known manner. As is also well known in the art, the syringe barrel 26 includes a hollow barrel tip 30 at the lowermost end thereof (see FIG. 2).

Located between the syringe 14 and the needle 12 is the hub member 16. As best seen in FIG. 2, the hub member 16 includes an axially extending bore 32 therein which is in communication with the bore 22 of the needle 12. The bore 32 is also in communication with the syringe barrel through the hollow barrel tip 30. The barrel tip 30 is secured to the upper portion of the hub member 16 by being force fit therearound or through the use of any conventional type of securing means such as an adhesive or screw thread or the like. Similarly, the upper hub end 24 is secured to the lower end of the hub 16 using any known conventional method.

The hub member 16 also includes a side port 34. Side port 34 extends outwardly and upwardly from the side of the hub member 16 intermediate the needle 12 and barrel 26. An auxiliary bore 36 extends entirely through the side port 34 from outside of the hub member 16 and into the axially extending bore 32 where it intersects the same at an acute angle relative to the axis of the axially extending bore.

Preferably, the upper end 38 of the side port is slightly enlarged to accommodate a pair of O-rings 40 and 42 therein. The O-rings 40 and 42 are maintained in place as shown in FIG. 2 through the use of recesses 44 and 46 formed in the inner wall of the enlarged portion 38 of the side port 34. An end cap 48 may also be applied to the uppermost end of the side port 34. The end cap 48 may either have a small hole formed in the center thereof or is easily pierceable so as to form a hole therein.

Guide wire 18 is, per se, conventional and may be comprised of a wound metal wire such as is known in the art. It has been found, however, that it is preferable to utilize a Teflon or silicone coated wire as this provides a better airtight seal than the wound metal wire. Guide wire 18 extends through the end cap 48 and the centers of the O-rings 40 and 42, through the auxiliary port 36 and into the needle bore 22 where it terminates adjacent the end 20 of the needle.

Prior to being used by the physician, the combined needle, syringe and guide wire combination 10 of the present invention is in the condition shown in FIG. 2. That is, the guide wire 18 is located within the auxiliary bore 36, hub bore 32 and needle bore 22, as shown. This can either be preassembled and delivered to the physician in this manner from the manufacturer or the physician or other person can preassemble the wire 18 into the position shown in FIG. 2 just prior to use.

The outer diameter of the guide wire 18 and the inner diameters of the O-rings 40 and 42 are chosen such that the guide wire 18 can be forced through the O-rings without any undue pressure. However, the O-rings contact the guide wires sufficiently so that, at least when the guide wire is not moving relative to the O-rings, there is a substantially airtight seal between the O-rings and the guide wire. And since the O-rings also seal against the inner wall of the side port, the O-rings function as a sealing means preventing air from entering the needle bore 22 from outside the side port when the guide wire is at rest within the auxiliary bore. As should be readily apparent to those skilled in the art, it is not necessary that the O-rings provide an airtight seal when the guide wire 18 is moving therethrough.

The combined syringe and needle arrangement of the present invention is utilized in the following manner. With the guide wire 18 in the position shown in FIG. 2, the physician inserts the needle tip 20 into the area of the vein. As he does this, he attempts to aspirate by drawing back on the plunger 28. If the vein has not been found, a significant amount of force will be required to draw the plunger 28 back. This is, of course, also due to the fact that the O-rings 40 and 42 provide an airtight seal in the side port 34. Without this airtight seal, the plunger 28 could be drawn back easily. The physician knows that he has penetrated the vein when blood flows easily into the syringe as he aspirates.

Once the vein is found, the physician need not remove the syringe barrel or any other part of the assembly. Rather, all that is necessary is for him to begin to slide the guide wire 18 forwardly until it enters the vein. And since the guide wire is preassembled so that its forward end is adjacent the sharpened end 20 of the needle 12, the guide wire 18 can be very quickly moved into the vein before the needle can be dislodged from its proper position. With the guide wire in place, the needle can be withdrawn in the known manner.

The present invention may be embodied in other specific forms without departing from the spirit or essential attributes thereof and accordingly reference should be made to the appended claims rather than to the foregoing specification as indicating the scope of the invention.

I claim:

1. A combined syringe and needle for introducing a guide wire into a human blood vessel comprising:
   a needle having a sharpened point at one end thereof and having a hollow bore extending from said sharpened end and through said needle to a hub end thereof;
   a syringe including a syringe barrel and a plunger, said barrel having a forward end adapted to be secured to a hub member;
   a hub member located between said syringe barrel and said needle and interconnecting said barrel and needle, said hub member including an axially extending bore therein in communication with said needle bore;
   said hub member further including a side port means intermediate said needle and said barrel, said side port means including an auxiliary bore therein which opens to the outside of said hub member, extends through said side port means and which intersects with said axially extending bore at an acute angle;
   an elongated guide wire, said guide wire extending from outside said hub member and into said auxiliary bore, and
   sealing means preventing air from entering said needle bore from outside said side port means when said guide wire is at rest within said auxiliary bore, said sealing means being comprised of said side port means having an enlarged portion therein and an elastomeric O-ring held in place within said enlarged portion, said guide wire passing through the center of said O-ring and being movable relative to said O-ring.

2. The invention as claimed in claim 1 wherein said sealing means is comprised of a pair of O-rings. portion.

3. The invention as claimed in claim 1 wherein said guide wire is a silicone-coated wire.

4. The invention as claimed in claim 1 wherein said guide wire is coated with Teflon.

5. The invention as claimed in claim 1 wherein said guide wire extends through said auxiliary bore and terminates within said needle bore.

* * * * *